(12) United States Patent
Nicholas et al.

(10) Patent No.: US 11,395,655 B2
(45) Date of Patent: Jul. 26, 2022

(54) HAND-HELD SURGICAL INSTRUMENTS

(71) Applicant: Covidien LP, Mansfield, MA (US)

(72) Inventors: David A. Nicholas, Trumbull, CT (US); Russell V. Pribanic, Roxbury, CT (US); Anthony D. Calderoni, Bristol, CT (US); John M. Pantazis, Stratford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/089,789

(22) Filed: Nov. 5, 2020

(65) Prior Publication Data

US 2021/0169476 A1    Jun. 10, 2021

Related U.S. Application Data

(60) Provisional application No. 62/944,400, filed on Dec. 6, 2019.

(51) Int. Cl.
*A61B 17/072* (2006.01)
*A61B 17/00* (2006.01)
*A61B 17/29* (2006.01)

(52) U.S. Cl.
CPC .... *A61B 17/072* (2013.01); *A61B 2017/0023* (2013.01); *A61B 2017/00398* (2013.01); *A61B 2017/00424* (2013.01); *A61B 2017/00734* (2013.01); *A61B 2017/07257* (2013.01); *A61B 2017/07271* (2013.01); *A61B 2017/07278* (2013.01); *A61B 2017/2923* (2013.01)

(58) Field of Classification Search
CPC ...................... A61B 17/072; A61B 2017/2923

USPC ....................................................... 227/175.1
See application file for complete search history.

(56) References Cited

U.S. PATENT DOCUMENTS

| 4,196,348 | A | 4/1980 | Iwakiri et al. |
| 4,803,362 | A | 2/1989 | Butts |
| 5,321,311 | A | 6/1994 | Umemura et al. |
| 5,465,895 | A * | 11/1995 | Knodel ............ A61B 17/07207 227/176.1 |
| 5,747,953 | A | 5/1998 | Philipp |
| 6,013,991 | A | 1/2000 | Philipp |
| 6,025,683 | A | 2/2000 | Philipp |
| 6,517,565 | B1 | 2/2003 | Whitman et al. |
| 6,960,894 | B2 | 11/2005 | Carusillo et al. |
| 7,638,958 | B2 | 12/2009 | Philipp et al. |
| 7,819,896 | B2 | 10/2010 | Racenet |
| 7,914,543 | B2 | 3/2011 | Roth et al. |

(Continued)

FOREIGN PATENT DOCUMENTS

| CN | 101227187 A | 7/2008 |
| CN | 203014768 U | 6/2013 |

(Continued)

OTHER PUBLICATIONS

European Search Report dated Jun. 8, 2021, issued in corresponding EP Appln. No. 20211928, 12 pages.

*Primary Examiner* — Michelle Lopez

(57) ABSTRACT

A handle assembly of a hand-held surgical instrument includes a handle housing, a rack supported in the handle housing and configured to operably couple to a driven member of a surgical end effector, an idler pinion gear operably coupled to the rack, and an output pinion gear drivingly coupled to a motor. The output pinion gear translates the rack via the idler pinion gear.

20 Claims, 5 Drawing Sheets

(56) References Cited

U.S. PATENT DOCUMENTS

| | | | |
|---|---|---|---|
| 8,480,703 B2 | 7/2013 | Nicholas et al. | |
| 8,968,276 B2 | 3/2015 | Zemlok et al. | |
| 9,283,054 B2 | 3/2016 | Morgan et al. | |
| 9,307,986 B2 | 4/2016 | Hall et al. | |
| 9,326,767 B2 | 5/2016 | Koch, Jr. et al. | |
| 9,358,003 B2 | 6/2016 | Hall et al. | |
| 9,398,911 B2 | 7/2016 | Auld | |
| 9,468,438 B2 | 10/2016 | Baber et al. | |
| 9,554,794 B2 | 1/2017 | Baber | |
| 9,597,104 B2 | 3/2017 | Nicholas et al. | |
| 9,654,050 B2 | 5/2017 | Kokinelis | |
| 9,693,774 B2 * | 7/2017 | Gettinger | A61B 17/07292 |
| 9,700,309 B2 | 7/2017 | Jaworek | |
| 9,700,318 B2 | 7/2017 | Scirica et al. | |
| 9,775,610 B2 | 10/2017 | Nicholas et al. | |
| 9,782,169 B2 | 10/2017 | Kimsey | |
| 9,782,187 B2 | 10/2017 | Zergiebel | |
| 9,801,646 B2 | 10/2017 | Zergiebel | |
| 9,991,069 B2 | 6/2018 | Nicholas et al. | |
| 2002/0062136 A1 | 5/2002 | Hillstead et al. | |
| 2004/0232197 A1* | 11/2004 | Shelton, IV | A61B 17/07207 227/175.1 |
| 2006/0278681 A1* | 12/2006 | Viola | A61B 17/00234 227/176.1 |
| 2009/0095790 A1 | 4/2009 | Whitman et al. | |
| 2009/0101692 A1* | 4/2009 | Whitman | A61B 17/068 227/175.1 |
| 2009/0108048 A1 | 4/2009 | Zemlok et al. | |
| 2009/0248041 A1 | 10/2009 | Williams et al. | |
| 2009/0283568 A1 | 11/2009 | Racenet et al. | |
| 2009/0314821 A1 | 12/2009 | Racenet | |
| 2010/0171026 A1 | 7/2010 | Saitou et al. | |
| 2010/0213240 A1 | 8/2010 | Kostrzewski | |
| 2011/0017801 A1 | 1/2011 | Zemlok et al. | |
| 2011/0121049 A1 | 5/2011 | Malinouskas et al. | |
| 2011/0204119 A1 | 8/2011 | McCuen | |
| 2012/0012638 A1 | 1/2012 | Huang | |
| 2012/0089131 A1 | 4/2012 | Zemlok et al. | |
| 2012/0130420 A1 | 5/2012 | Nicholas | |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2012/0303002 A1 | 11/2012 | Chowaniec et al. | |
| 2013/0126583 A1 | 5/2013 | Hueil et al. | |
| 2013/0184730 A1 | 7/2013 | Beardsley et al. | |
| 2013/0319706 A1 | 12/2013 | Nicholas et al. | |
| 2013/0324979 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2014/0246479 A1 | 9/2014 | Baber et al. | |
| 2014/0249557 A1 | 9/2014 | Koch, Jr. et al. | |
| 2014/0299647 A1 | 10/2014 | Scirica et al. | |
| 2014/0303668 A1 | 10/2014 | Nicholas et al. | |
| 2014/0305987 A1 | 10/2014 | Parihar | |
| 2014/0358129 A1 | 12/2014 | Zergiebel et al. | |
| 2015/0005788 A1 | 1/2015 | Sniffin et al. | |
| 2015/0105823 A1 | 4/2015 | Racenet et al. | |
| 2015/0235789 A1 | 8/2015 | Calderoni | |
| 2015/0374360 A1* | 12/2015 | Scheib | A61B 17/068 227/175.1 |
| 2015/0374372 A1 | 12/2015 | Zergiebel et al. | |
| 2016/0066916 A1 | 3/2016 | Overmyer et al. | |
| 2016/0100838 A1 | 4/2016 | Beaupre et al. | |
| 2016/0174978 A1 | 6/2016 | Overmyer et al. | |
| 2016/0324514 A1 | 11/2016 | Srinivas et al. | |
| 2017/0224333 A1 | 8/2017 | Hunter et al. | |
| 2017/0245854 A1 | 8/2017 | Zemlok et al. | |
| 2019/0000475 A1 | 1/2019 | Shelton, IV et al. | |
| 2019/0183594 A1 | 6/2019 | Shelton, IV et al. | |
| 2019/0261984 A1 | 8/2019 | Nelson et al. | |

FOREIGN PATENT DOCUMENTS

| | | |
|---|---|---|
| EP | 2055243 A2 | 5/2009 |
| EP | 2455007 A2 | 5/2012 |
| EP | 2777539 A2 | 9/2014 |
| EP | 2893882 A2 | 7/2015 |
| EP | 3011910 A1 | 4/2016 |
| KR | 20020020332 A | 3/2002 |
| KR | 20070000199 U | 2/2007 |
| WO | 2008147415 A1 | 12/2008 |
| WO | 2017123837 A2 | 7/2017 |

* cited by examiner

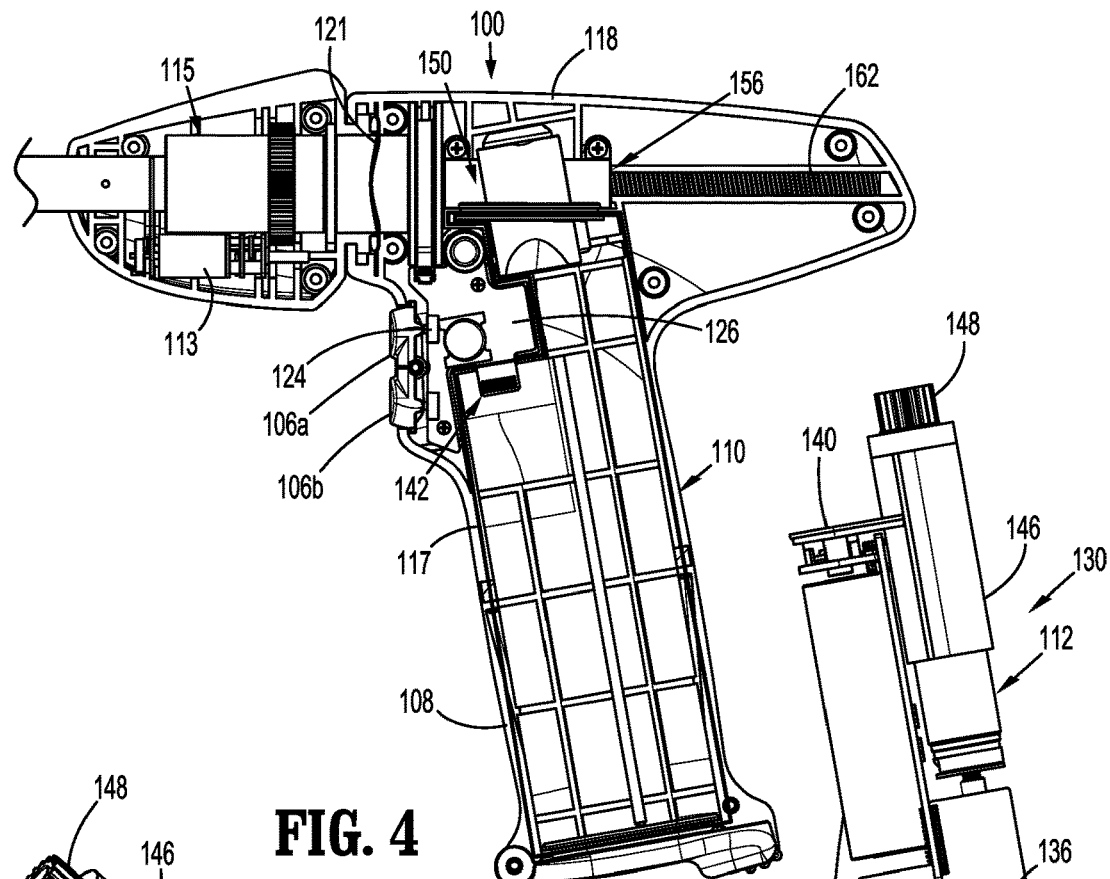
FIG. 4
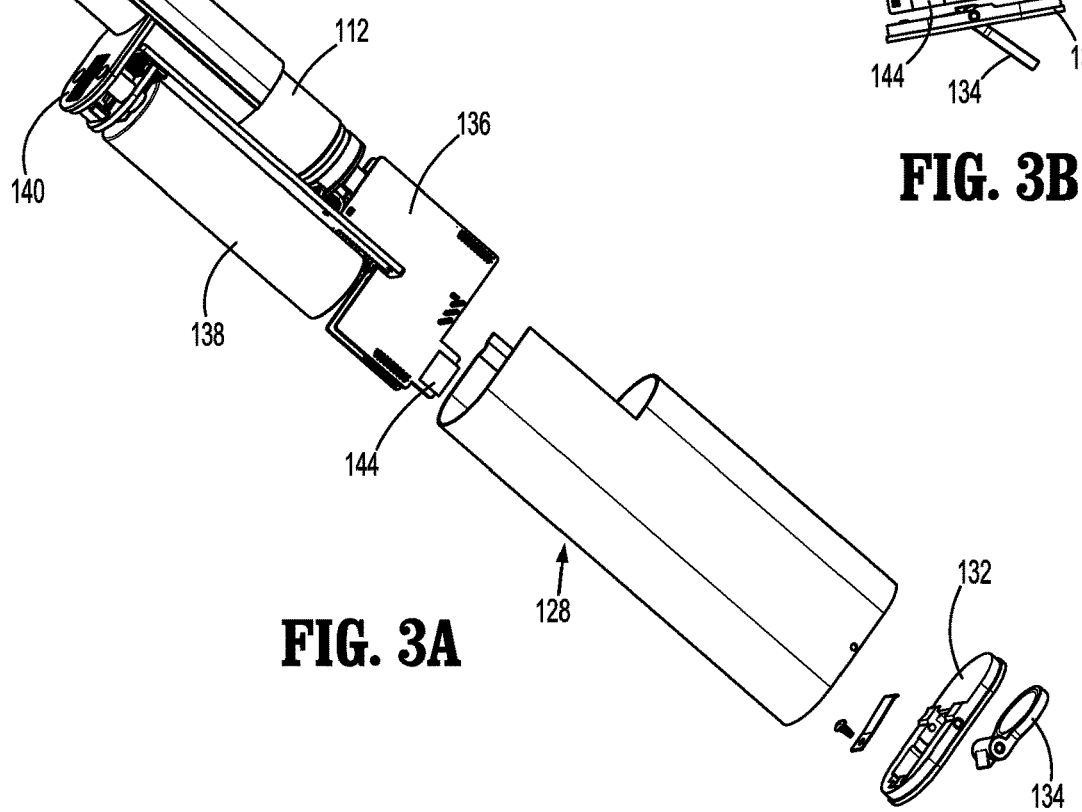
FIG. 3B
FIG. 3A

HAND-HELD SURGICAL INSTRUMENTS

CROSS-REFERENCE TO RELATED APPLICATIONS

The present application claims the benefit of and priority to U.S. Provisional Patent Application Ser. No. 62/944,400, filed on Dec. 6, 2019, the entire content of which being hereby incorporated by reference.

BACKGROUND

A number of handle assembly manufacturers have developed product lines with proprietary drive systems for operating and/or manipulating electromechanical surgical instruments. In many instances the electromechanical surgical instruments include a handle assembly, which is reusable, and disposable loading units and/or single use loading units, such as, for example, surgical end effectors that are selectively connected to the handle assembly prior to use and then disconnected from the handle assembly following use in order to be disposed of or in some instances sterilized for re-use.

SUMMARY

In one aspect of the present disclosure, a handle assembly of a hand-held surgical instrument is provided and includes a handle housing, a rack supported in the handle housing, an inner housing located within the handle housing, and an idler pinion gear. The rack is axially movable within the handle housing and configured to operably couple to a driven member of a surgical end effector. The idler pinion gear is supported in the inner housing and operably coupled to the rack. The idler pinion gear is configured to translate the rack.

In aspects, the handle housing may include a barrel portion, and a handle portion extending transversely and proximally from the barrel portion.

In some aspects, the rack may be located in the barrel portion and may define a longitudinal axis that is parallel with a longitudinal axis defined by the barrel portion.

In further aspects, the idler pinion gear may include an upper end portion engaged with the rack, and a lower end portion.

In other aspects, the idler pinion gear may define a recess located between the upper and lower end portions. The idler pinion gear may have an O-ring seal located in the recess.

In aspects, the idler pinion gear may be rotatable relative to and within the inner housing.

In some aspects, the lower end portion of the idler pinion gear may protrude from the inner housing.

In further aspects, the handle assembly may further include a motor configured to be located within the handle housing, and a pinion gear operably coupled to the motor and configured to engage the lower end portion of the idler pinion gear.

In other aspects, the inner housing may define a first longitudinally-extending channel. The rack may extend through the first channel.

In aspects, the inner housing may define a second channel extending transversely relative to the first channel and in communication with the first channel. The idler pinion gear may be received in the second channel.

In accordance with another aspect of the disclosure, a hand-held surgical instrument is provided and includes a handle housing, an instrument module configured for receipt in the handle housing, and a rack supported in the handle housing. The instrument module includes a motor and a gear operably coupled to the motor. The rack is supported in the handle housing and is axially movable within the handle housing. The rack is configured to operably couple to a driven member of a surgical end effector. The gear is configured to operable couple to the rack, such that a rotation of the gear results in a translation of the rack.

In aspects, the hand-held surgical instrument may further include an outer shell configured for receipt in the handle housing. The outer shell houses the instrument module therein.

In some aspects, the hand-held surgical instrument may further include an inner housing located within the handle housing. The inner housing may define a first channel having the rack extending therethrough.

In further aspects, the hand-held surgical instrument may further include an idler pinion gear supported in a second channel of the inner housing and operably coupled to the rack. The idler pinion gear may be configured to translate the rack in response to a rotation of the gear of the instrument module.

In other aspects, the hand-held surgical instrument may further include an idler pinion gear having an upper end portion engaged with the rack, and a lower end portion configured to engage the gear of the instrument module.

In aspects, the idler pinion gear may define a recess located between the upper and lower end portions. The idler pinion gear may have an O-ring seal located in the recess.

In some aspects, the instrument module may further include a battery for powering the motor.

In further aspects, the hand-held surgical instrument may further include a button movably coupled to the handle housing, and a printed circuit board. The button may be associated with the printed circuit board, and the battery may be detachably coupled to the printed circuit board, such that an actuation of the button activates the battery.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIG. 3A is a perspective view, with parts separated, illustrating the power assembly of FIG. 2 including a power assembly having an instrument module and an outer shell;

FIG. 3B is an assembled front view illustrating the instrument module of the power assembly of FIG. 3A;

FIG. 4 is a side view, with a housing half of the handle housing removed, illustrating internal components of the handle assembly;

DETAILED DESCRIPTION

Figure 1:
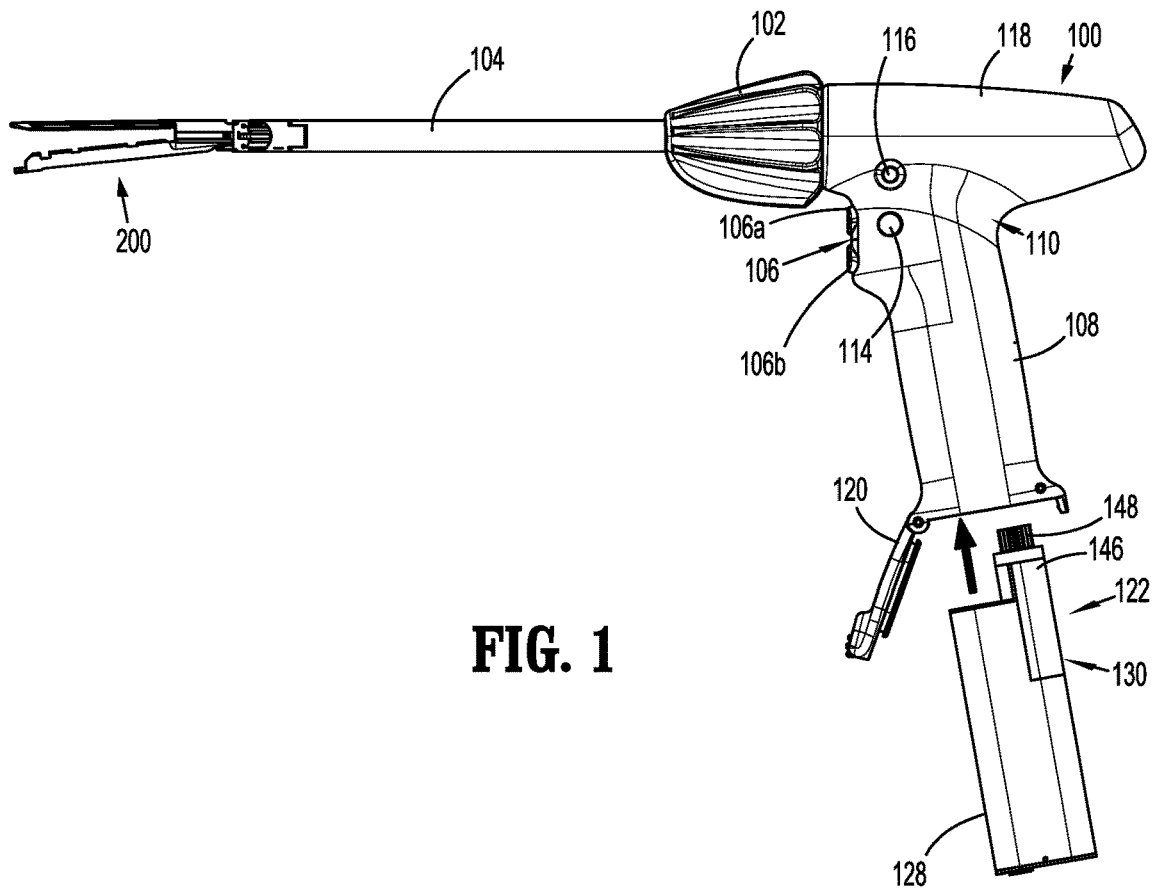
FIG. 1 is a side view illustrating a hand-held electromechanical surgical instrument including a handle assembly, with a power assembly shown separated, a shaft portion coupled to the handle assembly, and a surgical end effector coupled to the shaft portion.

Embodiments of the presently disclosed surgical instruments including handle assemblies thereof are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

As will be described in detail below, provided is a handle assembly of a hand-held surgical instrument having a motor-driven pinion gear and a rack operably coupled to the gear. The rack is configured to carry out a function of a surgical end effector coupled to the handle assembly in response to an actuation of the motor. Further provided is an ergonomic, disposable handle housing and a reusable power assembly (e.g., an instrument module housed within a sterile or non-sterile outer casing). Other features and benefits of the disclosed surgical instruments are further detailed below.

Figure 2:
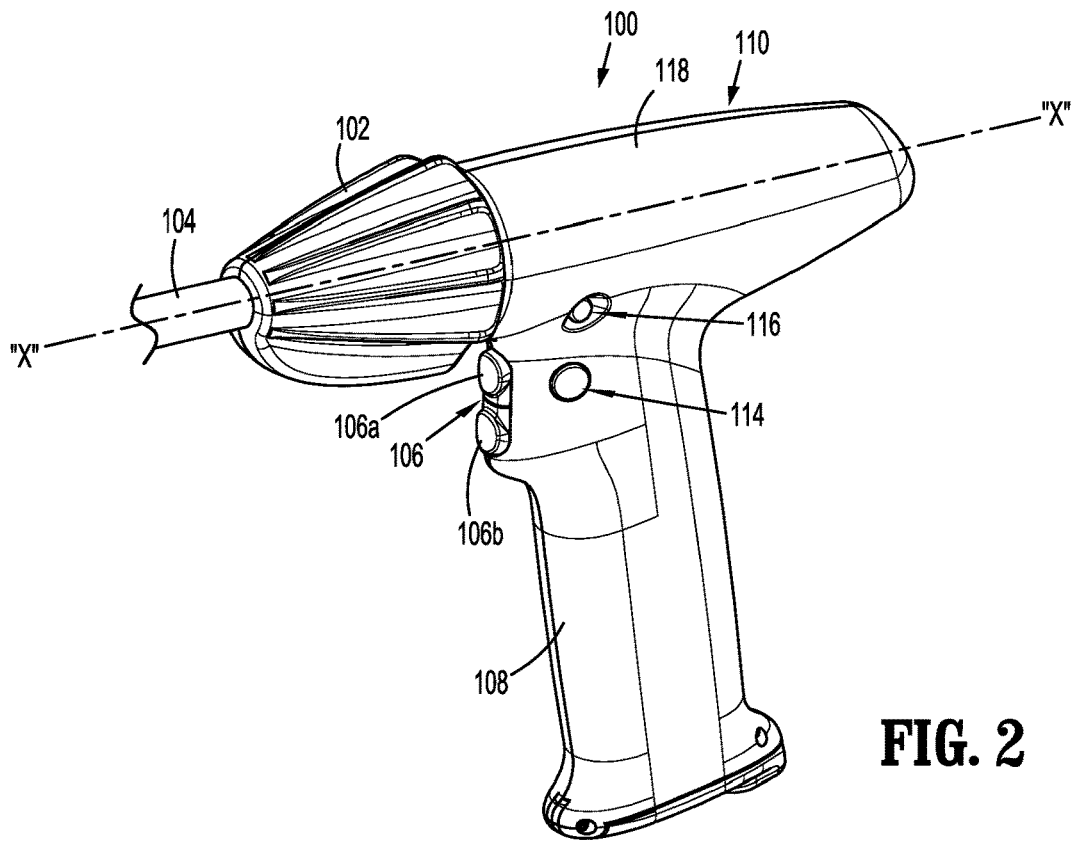
FIG. 2 is a partial perspective view illustrating a handle housing of the handle assembly of FIG. 1.
Figure 7:
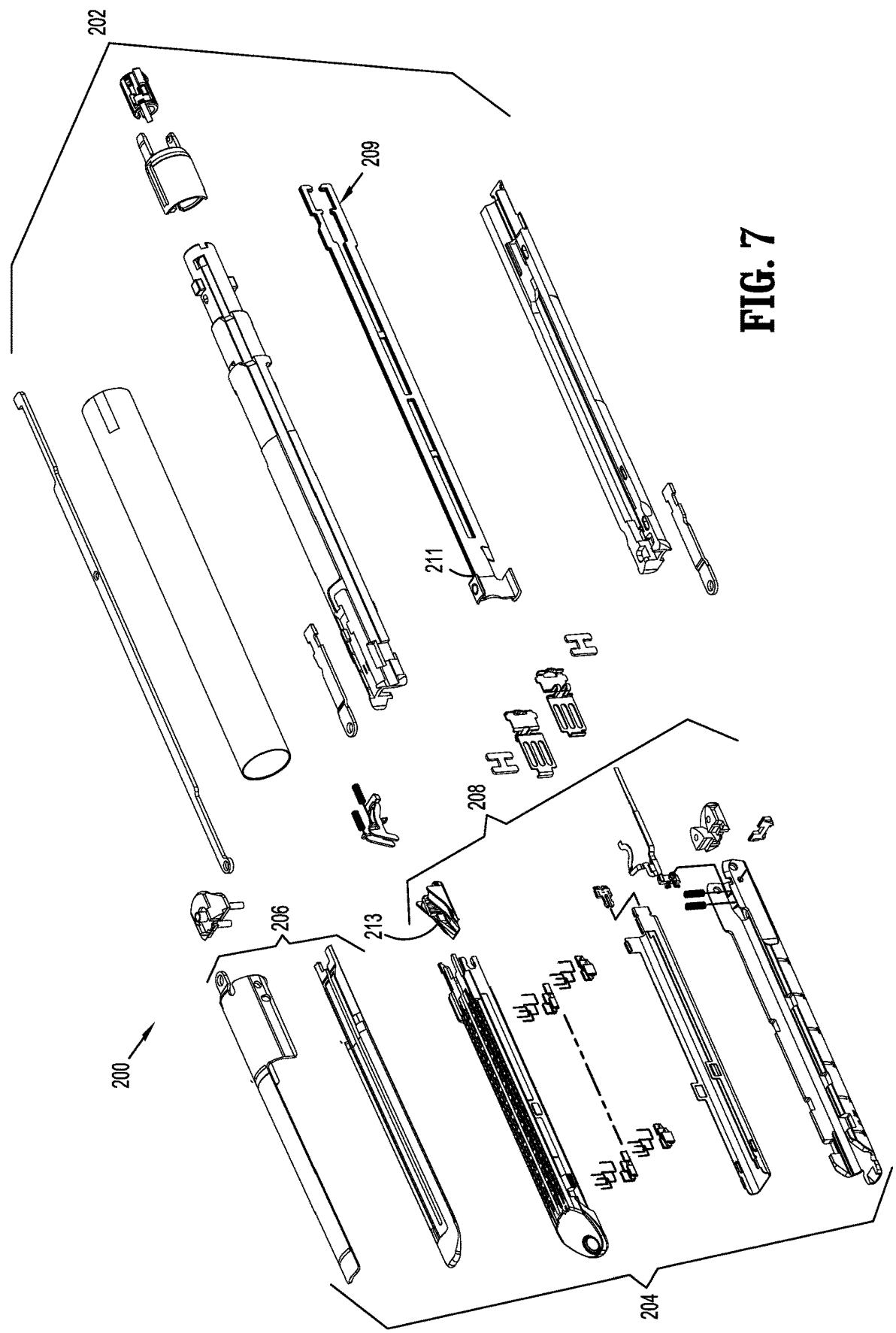
FIG. 7 is a perspective view, with parts separated, illustrating details of the surgical end effector of FIG. 1.

With reference to FIGS. 1 and 2, a surgical instrument, in accordance with an embodiment of the present disclosure, is generally designated as 10, and is in the form of a powered hand-held electromechanical surgical instrument configured for selective coupling thereto of a plurality of different surgical end effectors, for example, the surgical end effector 200 of FIGS. 1 and 7. The end effector 200 is configured for actuation and manipulation by the powered hand-held electromechanical surgical instrument 10. The hand-held electromechanical surgical instrument 10 includes a handle assembly 100, a knob housing 102 coupled to the handle assembly 100, and a shaft portion 104 extending distally from the knob housing 102 and configured for selective connection with a surgical attachment, such as, for example, the end effector 200.

The handle assembly 100 includes a disposable and sterile handle housing 110 having a body, such as, for example, a barrel portion 118, a handle portion 108 extending perpendicularly downward from the barrel portion 118 or transversely and proximally from the barrel portion 118, and a hinged door 120 pivotably coupled to the handle portion 108. The door 120 is selectively opened and closed to allow for the insertion or removal of a non-sterile power assembly 122. The handle portion 108 and the door 120 each have an inner periphery collectively defining a sterile barrier 117 (FIG. 4) for the power assembly 122 upon closing the door 120. In aspects, a proximal end portion or any suitable location of the barrel portion 118 may have a clear window (not shown) to allow for viewing of a display (e.g., an LCD, not shown).

The handle assembly 100 has a fire switch 106 configured and adapted to actuate the various functions of the end effector 200. The fire switch 106 may be constructed as a toggle bar pivotably coupled to the handle portion 108 of the handle housing 110. An activation of the fire switch 106 activates a motor 112 (FIGS. 3A and 3B) to advance or retract a firing rod (not explicitly shown) of the surgical instrument 10 depending on whether a top button 106a or a bottom button 106b of the fire switch 106 is actuated. The firing rod is coupled to a drive assembly 209 (FIG. 7) of the end effector 200 (which includes a knife rod 211 and an actuation sled 213), such that advancement of the firing rod advances the drive assembly 209 of the end effector 200, which closes the jaw members 206, 208 of the end effector 200 and fires the end effector 200 when a safety switch 116 is in an actuated state.

The handle assembly 100 has an articulation switch 114 extending transversely through the handle portion 108 and protruding outwardly from left and right sides of the handle portion 108. The articulation switch 114 is configured to actuate an articulation of the end effector 200 (e.g., move the end effector 200 along a horizontal plane between a position coaxial with the shaft portion 104 and multiple positions out of alignment with the shaft portion 104). The knob housing 102 is rotatably coupled to the handle housing 110 and has the shaft portion 104 non-rotationally coupled thereto. As such, a manual rotation of the knob housing 102 results in a corresponding rotation of the end effector 200 (e.g., the end effector 200 rotates about a central longitudinal axis "X" defined by the shaft portion 104). A wave spring 121 (FIG. 4) provides resistance to inadvertent rotation of the knob housing 102.

The handle assembly 100 may further include a safety switch 116 constructed as a tactile switch extending transversely through the barrel portion 118 of the handle housing 110. The safety switch 116 has opposing end portions exposed from an outer surface of the handle housing 110 to allow a clinician to slide the safety switch 116 between a firing-disabled position and a firing-enabled position. In the firing-disabled position, the safety switch 116 one of contacts or disengages a contact switch 124 (FIG. 4) on a printed circuit board 126 (FIG. 4) of the handle assembly 100, whereby a processor 136 of the power assembly 122 is signaled to prevent an activation of the motor 112 notwithstanding an actuation of the fire switch 106. In the firing-enabled position, the safety switch 116 contacts or disengages the contact switch 124, whereby the processor 136 is signaled to allow an activation of the motor 112 upon actuating the fire switch 106. In aspects, the safety switch 116 may have a light therein configured to blink or remain on in a steady state to indicate the position of the safety switch 116.

In some embodiments, the switches 106, 114, 116 of the handle assembly 100 may be assigned to actuate various functions to be carried out by various surgical end effectors. It is contemplated that the switches 106, 114, 116 can be variously configured, such as, for example, as switches, rockers, flaps, latches, levers, dials, buttons, or touch screens.

With reference to FIGS. 1, 3A, 3B, and 4, the reusable power assembly 122 of the handle assembly 100 includes a sterile outer shell 128 and a reusable instrument module 130 configured for removably receipt in the outer shell 128. The outer shell 128 has a cover 132 received in an open bottom end of the outer shell 128, and a spring-loaded pull tab 134 to facilitate removal of the cover 132. The instrument module 130 includes the motor 112, such as, for example, an electrical drive motor, which is electrically connected or wirelessly connected to the motor controller or processor 136 and a battery 138. In aspects, the battery 138 may include a boost circuit and may be rechargeable (e.g., wirelessly). The battery 138 has a card edge connector 140 configured for detachable receipt of a card edge header 142 of the printed circuit board 126 to allow for communication from the fire switch 106, the safety switch 116, the articulation switch 114, and an articulation encoder to the battery 138. The processor 136 may include a USB charging connector 144 to allow for the battery 138 to be recharged with a USB charger or wirelessly (e.g., via induction).

The instrument module 130 further includes a gearbox 146, such as, for example, a planetary gearbox, operably coupled to the drive motor 112, and an output gear 148, such as, for example, a pinion gear, drivingly coupled to the gearbox 146 and configured to rotate about a longitudinal axis defined by the gearbox 146. The planetary gearbox 146 multiplies torque while reducing speed.

All components of the instrument module 130 other than an upper portion of the planetary gear box 146 and the pinion gear 148 are concealed within the outer shell 128. Rotation of the pinion gear 148 by the motor 112 functions to drive shafts and/or gear components of the handle assembly 100 in order to perform the various operations of the end effector 200 (FIG. 7). For example, the motor 112 is configured to move jaw members 206, 208 (FIG. 7) of the end effector 200 relative to one another and to fire staples from the end effector 200.

Figure 5:
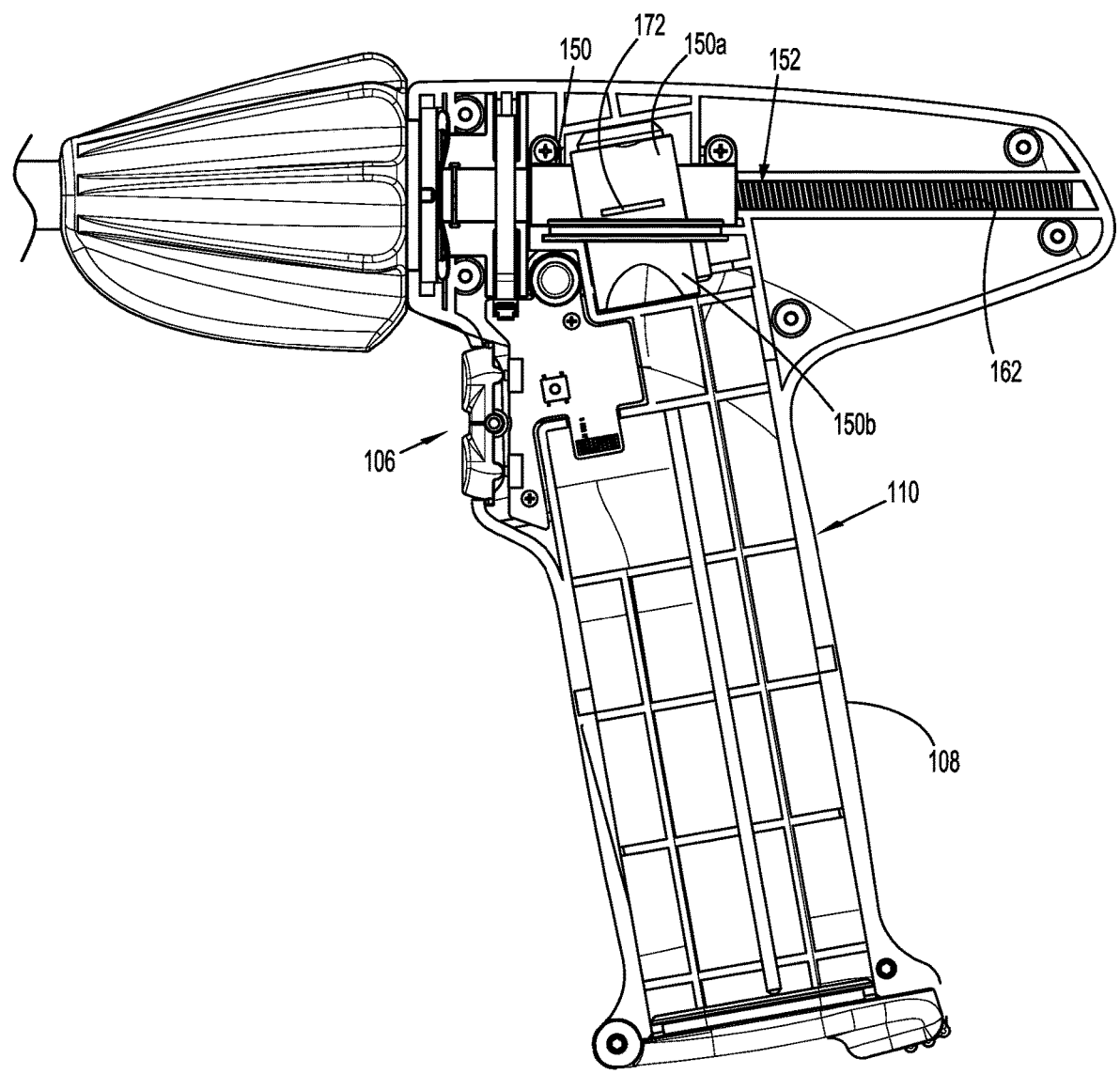
FIG. 5 is an enlarged side view, with a housing half of the handle housing and power assembly removed, illustrating internal components of the handle assembly of FIG. 2.
Figure 6:
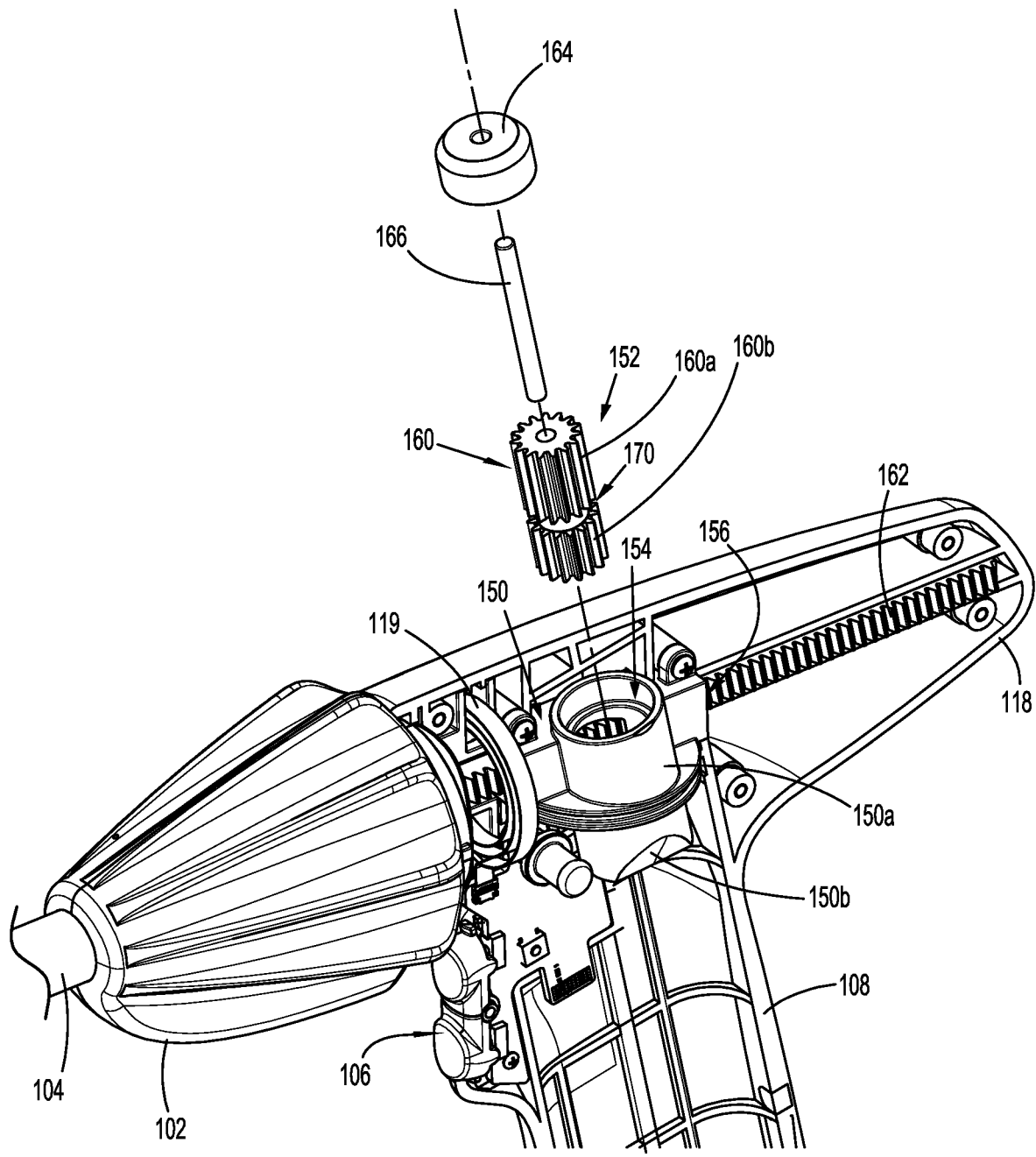
FIG. 6 is a partial perspective view, with parts separated, illustrating details of a rack and pinion assembly of the handle assembly of FIG. 2.

With reference to FIGS. 4-6, the handle assembly 100 includes an inner housing 150 and a rack and pinion assembly 152. The inner housing 150 of the handle assembly 100 is fixed within the barrel portion 118 of the handle housing 110 and includes a top end portion 150a and a bottom end portion 150b. The inner housing 150 defines a first channel 154 extending vertically through the upper and lower end portions 150a, 150b thereof. The first channel 154 may have a cylindrical configuration or any other suitable shape to allow for rotation therein of an idler pinion gear 160 of the rack and pinion assembly 152. The inner housing 150 further defines a second channel 156 extending horizontally through the upper end portion 150a thereof. The second channel 156 may have a rectangular shape or any other suitable shape to allow for translation therethrough of a rack 162 of the rack and pinion assembly 152. The second channel 156 is in communication with the first channel 154, such that the idler pinion gear 160 and rack 162 can engage one another.

The rack and pinion assembly 152 further includes a cap 164 fixed to the upper end portion 150a of the inner housing 150 and a pin 166 fixed to the cap 164 and extending through the first channel 154 of the inner housing 150. The idler pinion gear 160 is located about the pin 166 and is received in the first channel 154 of the inner housing 150. The idler pinion gear 160 has an upper end portion 160a and a bottom end portion 160b monolithically formed with or integrally connected to one another. The bottom end portion 160b of the idler pinion gear 160 is configured to protrude beyond the bottom end portion 150b of the inner housing 150 to selectively engage the output pinion gear 148 (FIGS. 3A and 3B) of the instrument module 130 when the power assembly 122 is received in the handle portion 108 of the handle housing 110. The top end portion 160a of the idler pinion gear 160 is located in the upper end portion 150a of the inner housing 150 and is engaged with teeth of the rack 162.

The idler pinion gear 160 defines an annular recess 170 between the upper and lower end portions 160a, 160b thereof. The annular recess 170 receives an O-ring seal 172 (FIG. 5) therein. The O-ring seal 172 is captured in an inner annular groove (not explicitly shown) defined in the inner housing 150. The idler pinion gear 160 is axially supported in the first channel 154 of the inner housing 150 while for rotation of the idler pinion gear 160 in the first channel 154 of the inner housing 150.

The rack 162 of the rack and pinion assembly 152 is disposed in the barrel portion 118 of the handle housing 110 and extends parallel with the barrel portion 118. The rack 162 extends through the second channel 156 of the inner housing 150 and has a distal end portion (not explicitly shown) configured to operably couple to the drive assembly 209 (FIG. 7) of the end effector 200. The rack 162 is operably coupled to the output pinion gear 148 (FIGS. 3A and 3B) via the upper end portion 160a of the idler pinion gear 160. In aspects, the rack 162 may be directly engaged to the output pinion gear 148.

With reference to FIG. 7, the end effector 200 may be configured to be coupled to a distal end of the shaft portion 104 of the surgical instrument 10. The end effector 200 includes a proximal body portion 202 and a tool assembly 204. The proximal body portion 202 is releasably attached to the handle portion 102 and the tool assembly 204 is pivotally attached to a distal end of the proximal body portion 202 of the end effector 200. The proximal body portion 202 is configured to articulate relative to the distal end of the shaft portion 102 via actuation of an articulation motor 113 (FIG. 4) and an associated articulation assembly 115. A flex circuit coil 119 (FIG. 6) is coupled to the articulation motor 113 to maintain electrical communication between the articulation motor 113 and the printed circuit board 126 while allowing for rotation of the knob housing 102. The tool assembly 204 includes an anvil assembly 206 and a cartridge assembly 208. The cartridge assembly 208 is pivotal in relation to the anvil assembly 206 and is movable between an open or unclamped position and a closed or clamped position for insertion through a cannula of a trocar.

For a detailed discussion of the construction and operation of the surgical end effector 200, as illustrated in FIGS. 1 and 7, reference may be made to U.S. Pat. No. 7,819,896, filed on Aug. 31, 2009, entitled "TOOL ASSEMBLY FOR A SURGICAL STAPLING DEVICE," the entire contents of which being incorporated by reference herein.

In operation, the power assembly 122 is inserted into the handle portion 108 of the handle housing 110 and the door 120 is closed, thereby sealing the non-sterile power assembly 122 in the sterile handle portion 108. The card edge head 142 of the printed circuit board 126 is connected to the card edge connector 140 of the instrument module 130. Upon properly inserting the power assembly 122, the output pinion gear 148 of the instrument module 130 meshingly engages the bottom end portion 160b of the idler pinion gear 160.

To operate the surgical end effector 200, the fire switch 106 may be toggled, whereby the battery 138 provides power to the motor 112, which drives a rotation of the output pinion gear 148 via the gearbox 146. As the output pinion gear 112 rotates in a first direction, the idler pinion gear 148 rotates in an opposite second direction, to translate the rack 162 along the longitudinal axis of the barrel portion 118 of the handle housing 110. Since the rack 162 is operably coupled to the drive assembly 209 of the surgical end effector 200, translation of the rack 162 results in one of an opening or closing of the jaw members 206, 208 depending on the direction of translation of the rack 162. To fire staples from the surgical end effector 200, the safety switch 116 is actuated, and then the bottom button 106b of the fire switch 106 is actuated, whereby the sled 213 of the surgical end effector 200 translates through the cartridge assembly 208 to fire the staples into tissue.

Any of the components described herein may be fabricated from either metals, plastics, resins, composites or the like taking into consideration strength, durability, wearability, weight, resistance to corrosion, ease of manufacturing, cost of manufacturing, and the like. Any of the gears disclosed herein may be configured as any suitable gear, such as bevel gears, spur gears, spiral gears, worm gears, or the like.

It will be understood that various modifications may be made to the embodiments of the presently disclosed surgical instruments including switch assemblies. Therefore, the above description should not be construed as limiting, but merely as exemplifications of embodiments. Those skilled in the art will envision other modifications within the scope and spirit of the present disclosure.

What is claimed is:

1. A handle assembly of a hand-held surgical instrument, comprising:
   a handle housing;
   a rack supported in the handle housing and axially movable within the handle housing, the rack configured to operably couple to a driven member of a surgical end effector;
   an inner housing located within the handle housing; and
   an idler pinion gear supported in the inner housing and operably coupled to the rack, wherein the idler pinion gear is configured to translate the rack.

2. The handle assembly according to claim 1, wherein the handle housing includes a barrel portion, and a handle portion extending transversely and proximally from the barrel portion.

3. The handle assembly according to claim 2, wherein the rack is located in the barrel portion and defines a longitudinal axis that is parallel with a longitudinal axis defined by the barrel portion.

4. The handle assembly according to claim 1, wherein the idler pinion gear includes an upper end portion engaged with the rack, and a lower end portion.

5. The handle assembly according to claim 4, wherein the idler pinion gear defines a recess located between the upper and lower end portions, the idler pinion gear having an O-ring seal located in the recess.

6. The handle assembly according to claim 5, wherein the idler pinion gear is rotatable relative to and within the inner housing.

7. The handle assembly according to claim 4, wherein the lower end portion of the idler pinion gear protrudes from the inner housing.

8. The handle assembly according to claim 7, further comprising:
   a motor configured to be located within the handle housing; and
   a pinion gear operably coupled to the motor and configured to engage the lower end portion of the idler pinion gear.

9. The handle assembly according to claim 1, wherein the inner housing defines a first longitudinally-extending channel, the rack extending through the first channel.

10. The handle assembly according to claim 9, wherein the inner housing defines a second channel extending transversely relative to the first channel and in communication with the first channel, the idler pinion gear received in the second channel.

11. A hand-held surgical instrument, comprising:
    a handle housing;
    an instrument module configured for receipt in the handle housing and including:
      a motor; and
      a gear operably coupled to the motor;
    a rack supported in the handle housing and axially movable within the handle housing, the rack configured to operably couple to a driven member of a surgical end effector, wherein the gear is configured to operably couple to the rack, such that a rotation of the gear results in a translation of the rack; and
    an inner housing located within the handle housing, the inner housing defining a first channel having the rack extending therethrough.

12. The hand-held surgical instrument according to claim 11, further comprising an outer shell configured for receipt in the handle housing, wherein the outer shell houses the instrument module therein.

13. The hand-held surgical instrument according to claim 11, further comprising an idler pinion gear supported in a second channel of the inner housing and operably coupled to the rack, wherein the idler pinion gear is configured to translate the rack in response to a rotation of the gear of the instrument module.

14. The hand-held surgical instrument according to claim 11, wherein the handle housing includes a barrel portion, and a handle portion extending transversely and proximally from the barrel portion.

15. The hand-held surgical instrument according to claim 14, wherein the rack is located in the barrel portion and defines a longitudinal axis that is parallel with a longitudinal axis defined by the barrel portion.

16. The hand-held surgical instrument according to claim 11, further comprising an idler pinion gear including an upper end portion engaged with the rack, and a lower end portion configured to engage the gear of the instrument module.

17. The hand-held surgical instrument according to claim 16, wherein the idler pinion gear defines a recess located between the upper and lower end portions, the idler pinion gear having an O-ring seal located in the recess.

18. The hand-held surgical instrument according to claim 11, wherein the instrument module further includes a battery for powering the motor.

19. The hand-held surgical instrument according to claim 18, further comprising:
    a button movably coupled to the handle housing; and
    a printed circuit board, the button associated with the printed circuit board, and the battery detachably coupled to the printed circuit board, such that an actuation of the button activates the battery.

20. A hand-held surgical instrument, comprising:
    a handle housing;
    an instrument module configured for receipt in the handle housing and including:
      a motor; and
      a gear operably coupled to the motor;
    a rack supported in the handle housing and axially movable within the handle housing, the rack configured to operably couple to a driven member of a surgical end effector, wherein the gear is configured to operably couple to the rack, such that a rotation of the gear results in a translation of the rack; and
    an idler pinion gear including an upper end portion engaged with the rack, and a lower end portion configured to engage the gear of the instrument module, wherein the idler pinion gear defines a recess located between the upper and lower end portions, the idler pinion gear having an O-ring seal located in the recess.

* * * * *